United States Patent [19]

Sogard et al.

[11] Patent Number: 4,944,745
[45] Date of Patent: Jul. 31, 1990

[54] PERFUSION BALLOON CATHETER

[75] Inventors: David J. Sogard, Minneapolis; Scott Savitt, Eden Prairie, both of Minn.

[73] Assignee: SciMed Life Systems, Inc., Maple Grove, Minn.

[21] Appl. No.: 162,003

[22] Filed: Feb. 29, 1988

[51] Int. Cl.⁵ .............................................. A61M 25/00
[52] U.S. Cl. ..................................... 606/194; 604/53; 604/96; 604/103
[58] Field of Search ........................... 604/53, 96-103, 604/280, 282; 128/344; 606/192, 193, 194

[56] References Cited

U.S. PATENT DOCUMENTS

| | | | |
|---|---|---|---|
| 2,930,377 | 3/1960 | Cowley | 128/344 |
| 3,435,824 | 4/1969 | Gamponia | 128/344 |
| 3,769,981 | 11/1973 | McWhorter | 128/349 |
| 3,889,685 | 6/1975 | Miller, Jr. et al. | 128/348 |
| 3,889,686 | 6/1975 | Duturbure | 128/349 |
| 4,195,637 | 4/1980 | Grüntzig | 128/348 |
| 4,198,981 | 4/1980 | Sinnreich | 128/344 |
| 4,230,119 | 10/1980 | Blum | 128/325 |
| 4,329,993 | 4/1982 | Lieber et al. | 128/349 |
| 4,423,725 | 1/1984 | Baran et al. | 128/207 |
| 4,447,227 | 4/1984 | Kotsanis | 604/95 |
| 4,581,017 | 4/1986 | Sahota | 604/101 |
| 4,597,755 | 7/1986 | Samson et al. | 604/96 |
| 4,646,742 | 3/1987 | Packard et al. | 128/344 |
| 4,661,094 | 4/1987 | Simpson | 604/53 |
| 4,748,982 | 6/1988 | Horzewski et al. | 128/344 |
| 4,762,129 | 8/1988 | Bonzel | 128/344 |
| 4,763,654 | 8/1988 | Jang | 604/101 |
| 4,771,777 | 9/1988 | Horzewki et al. | 604/102 |
| 4,790,315 | 12/1988 | Mueller, Jr. et al. | 128/344 |
| 4,820,271 | 4/1989 | Deutsch | 128/344 |
| 4,832,028 | 5/1989 | Patel | 128/344 |

| | | | |
|---|---|---|---|
| 4,877,031 | 10/1989 | Conway et al. | 604/96 |

FOREIGN PATENT DOCUMENTS 3010743 3/1980 Fed. Rep. of Germany .
86/03129 5/1986 PCT Int'l Appl. .

OTHER PUBLICATIONS

Erbel, Raimund et al., "New Balloon Catheter for Prolonged Percutaneous Transluminal Coronary Angioplasty and Bypass Flow in Occluded Vessels", *Catheterization and Cardiovascular Diagnosis,* 12:116-123 (1986).

*Primary Examiner*—Stephen C. Pellegrino
*Assistant Examiner*—Ralph Lewis
*Attorney, Agent, or Firm*—Kinney & Lange

[57] ABSTRACT

A passive perfusion balloon catheter for performing percutaneous transluminal coronary angioplasty allows prolonged dilatations without blocking blood flow through the artery being treated. The passive perfusion balloon catheter includes a dual lumen shaft, a balloon head connected to the distal end of the dual lumen shaft, a balloon mounted around the balloon head, and a distal tip which is connected to and extends distally from balloon. The balloon head defines a blood flow channel through which blood can flow when the balloon is inflated. The blood flow channel is generally aligned with a guide wire lumen of the dual lumen shaft so that a guide wire can extend through the catheter and out the distal tip, and can be partially withdrawn into the guide wire lumen to permit perfusion while the balloon is inflated. If necessary, the guide wire can be reinserted from the guide wire lumen through the flow passage so that the wire can be left in place while the catheter is removed.

44 Claims, 3 Drawing Sheets

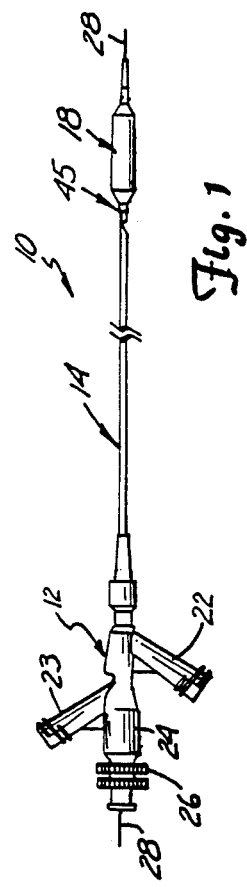
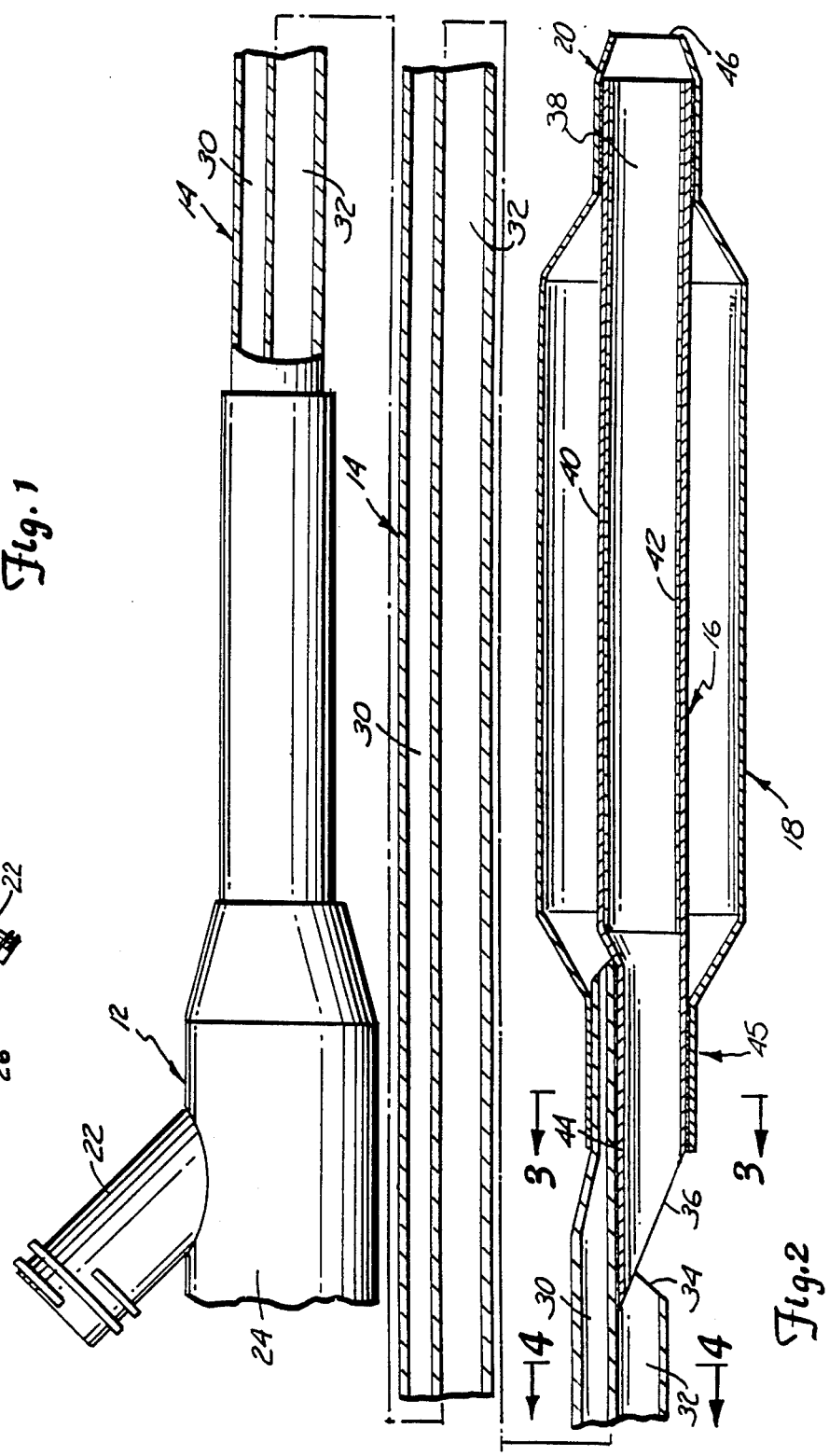

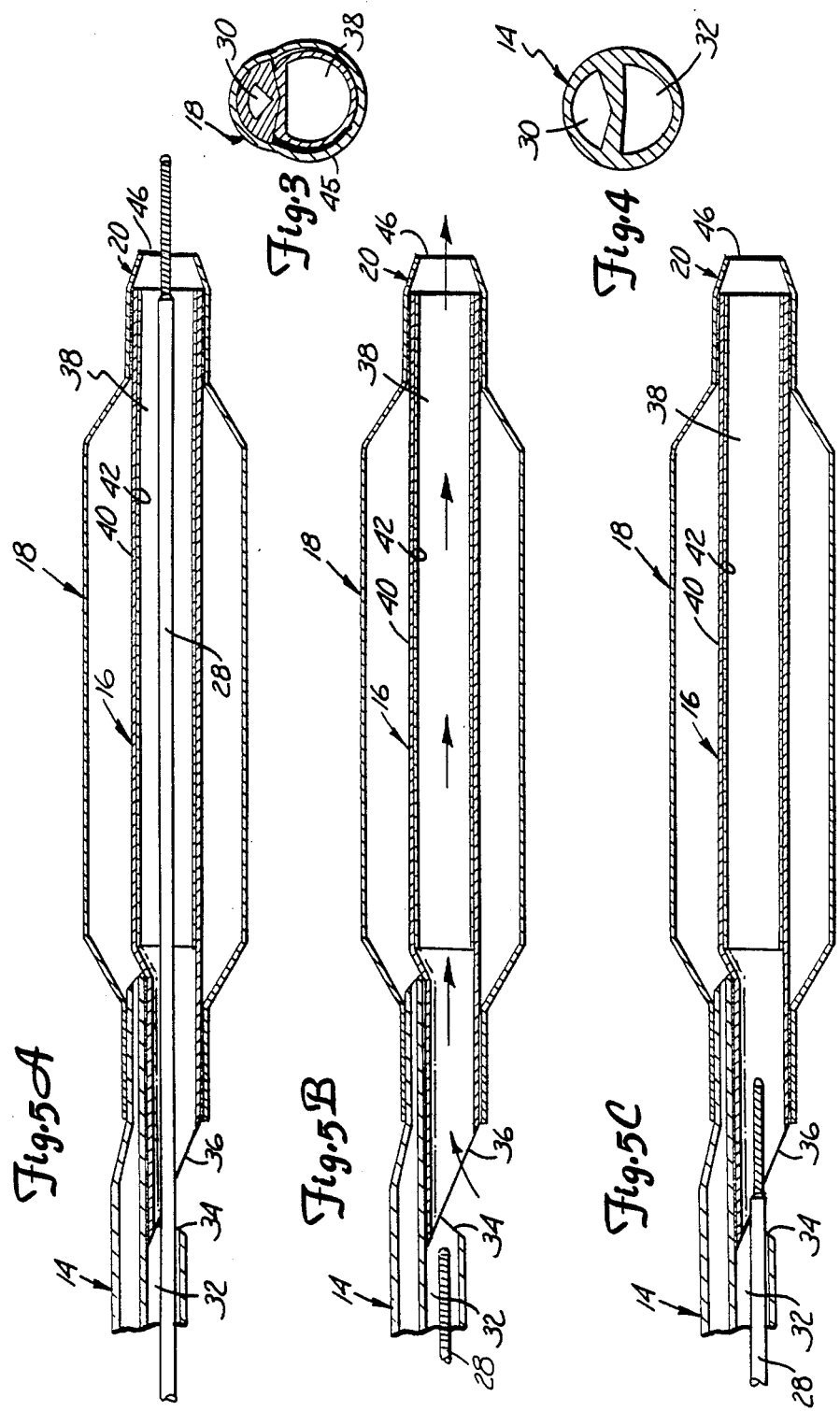

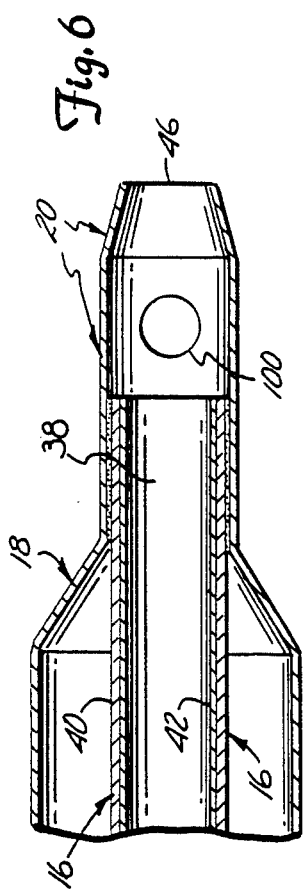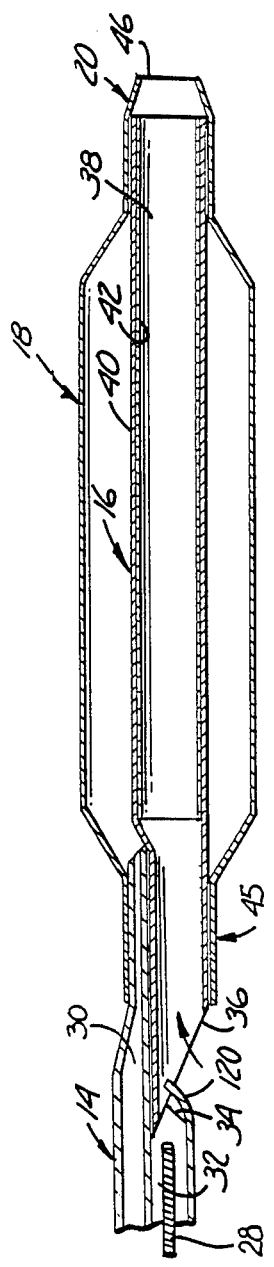

PERFUSION BALLOON CATHETER

BACKGROUND OF THE INVENTION

1. Field of the Invention.

The present invention relates to the field of angioplasty. In particular, the present invention relates to a balloon catheter which provides prolonged dilatations without blocking blood flow by use of passive perfusion.

2. Description of the Prior Art.

Angioplasty has gained wide acceptance in recent years as an efficient and effective method for treating types of vascular diseases. In particular, angioplasty is widely used for opening stenoses in coronary arteries, although it is also used for treatment of stenoses in other parts of the vascular system. The most widely used form of angioplasty is called percutaneous transluminal coronary angioplasty (PTCA) and makes use of a dilatation catheter which has an inflatable balloon at its distal end. Using fluoroscopy, the physician guides the catheter through the vascular system until the balloon is positioned across the stenosis. The balloon is then inflated by supplying fluid under pressure through an inflation lumen to the balloon. The inflation of the balloon opens the artery to reestablish acceptable blood flow through the artery.

An initial concern about PTCA was the temporary blockage of blood flow during balloon inflation. As cardiologists gained clinical experience with PTCA, the concern with temporary blood flow blockage declined; the vast majority of patients tolerate 30 to 60 second dilatations quite well. Concurrently, cardiologists discovered that prolonged dilatations can help overcome certain kinds of complications encountered with the angioplasty. Prolonged dilatations of several minutes are used to deal with dissections, intimal flaps, acute thrombosis and vessel spasms. The profound ischemia of a long dilatation is outweighed by the potential prevention of emergency coronary bypass surgery.

In the prior art, methods for enabling prolonged dilatations have been cumbersome, have been experimental, or have had potentially harmful side effects. Consequently, there has been no definitive study of the effects of prolonged dilations on the efficacy of PTCA.

In order to perform prolonged dilatations, several approaches have been suggested. These include the use of pharmacologic agents to improve myocardial tolerance of ischemia, synchronized retroprofusion, mechnical pump distal perfusion, and auto or passive perfusion.

The use of pharmacologic agents treats the symptoms of ischemia, but not the cause. As a result, this approach is inherently limited.

Synchronized retroprofusion involves pumping blood during diastole into the coronary sinus and then subselectively into the regional coronary veins which drain the jeopardized myocardium. This approach potentially offers nearly complete myocardial perfusion. The disadvantage of synchronized retroprofusion, however, is that it is complicated and cumbersome.

Mechanical pump distal perfusion involves pumping blood (or other perfusate) through a lumen of the PTCA catheter. The need to pump through the PTCA catheter requires some form of mechanical pump, and complicates the angioplasty equipment and procedure.

With passive perfusion, the balloon catheter acts as a temporary stent. Passive or auto perfusion catheters which have been proposed in the past have used a design similar to "bail out" catheters: side holes in the catheter through-lumen proximal and distal to the balloon. These catheters, however, have several limitations. First, blood flow through the balloon may be suboptimal for many clinical situations (such as distal lesions and hypotension). Second, this configuration presents the problem of catheter initiated thrombus, for which no satisfactory solution has emerged. Third, the crossing profiles of these catheters typically require two step angioplasty—the lesion is first opened with a low profile catheter, which then must be exchanged with a perfusion balloon for a long dilatation period.

SUMMARY OF THE INVENTION

The perfusion balloon catheter of the present invention includes a multiple lumen shaft, a balloon head connected to a distal end of the shaft, a balloon mounted around the balloon head, and a distal tip which extends distally from the balloon. The balloon head defines a longitudinal blood flow channel through which blood can flow when the balloon is inflated. The blood flow channel is generally aligned with a guide wire lumen of the shaft so that a guide wire can extend through the catheter and out the distal tip, and can be partially withdrawn into the guide wire lumen to permit perfusion through the blood flow channel while the balloon is inflated.

BRIEF DESCRIPTION OF THE DRAWINGS

FIG. 1 shows a preferred embodiment of the passive perfusion balloon catheter of the present invention.

FIG. 2 is a cross-sectional view of a distal portion of the passive perfusion balloon catheter of FIG. 1.

FIG. 3 is a sectional view along Section 3—3 of FIG. 2.

FIG. 4 is a sectional view along Section 4—4 of FIG. 2.

FIGS. 5A, 5B, 5C are cross-sectional views of the passive perfusion balloon catheter showing a guide wire extending through the balloon head and out the distal tip, showing the guide wire in a retracted position to permit perfusion through the balloon head, and showing the guide wire during reinsertion through the balloon head, respectively.

FIG. 6 shows a sectional view of a distal portion of another embodiment of the present invention.

FIG. 7 is a partial sectional view showing still another embodiment.

DETAILED DESCRIPTION OF THE PREFERRED EMBODIMENTS

Passive perfusion balloon catheter 10 shown in FIGS. 1 and 2 includes five major elements: manifold 12, shaft 14, balloon head 16 (FIG. 2), balloon 18, and distal tip 20.

Manifold 12 includes inflation port 22, through port 23 and guide wire port 24. Hemostasis valve 26 is mounted on guide wire port 24. In FIG. 1, guide wire 28 extends through guide wire port 24, shaft 14, balloon head 16, and distal tip 20.

Shaft 14 is a multilumen tube. In preferred embodiments, shaft 14 is a dual lumen polyethylene tube containing inflation lumen 30 and guide wire lumen 32. At its distal end, inflation lumen 30 is in communication with the interior of balloon 18. Radiopaque fluid is supplied under pressure from an inflation device (not shown) which is connected to inflation port 22 of manifold 12.

Guide wire lumen 32 extends from guide wire port 24 to distal opening or cut-away 34 which is positioned adjacent proximal opening 36 of balloon head 16. Through port 23 communicates also with wire lumen 32.

Balloon head 16 forms a substrate or platform for balloon 18. Balloon head 16 defines a main blood flow channel which extends longitudinally through balloon 18. Balloon head 16 is preferably formed by a polyolefin tube 40 which is reinforced by helically wound metal coil 42. As shown in FIG. 2, coil 42 extends from the distal end of balloon head 16 to a position near the proximal end of balloon head 16 to provide additional strength to prevent collapse of balloon head tubing 40 due to the pressure of the fluid supplied to the interior of balloon 18 during inflation. Coil 42 provides this additional collapse resistance without sacrificing flexibility, and while decreasing kinkability. Coil 42 also acts as a radiopaque marker. The use of coil 42 also permits a thin wall construction to maximize the size of the flow passage without sacrificing profile.

Proximal portion 44 of tubing 40 has a reduced profile and is shaped to receive a distal portion of inflation lumen 30. As best shown in FIGS. 2 and 3, inflation lumen 30 extends beyond guide wire lumen 32 and has a reduced profile in proximal bond area 45 where balloon head 16, inflation lumen 30, and proximal portion 44 of tubing 40 are all bonded together. This bond is formed by suitable adhesive, such as an epoxy.

Balloon 18, which is shown in its inflated state in FIGS. 1 and 2, is bonded near its distal end to a distal end portion of balloon head 16. The bond is formed, in preferred embodiments, by a suitable adhesive such as epoxy.

Distal tip 20 is, in the embodiment shown in FIG. 2, an integral extension of balloon 18. Tip 20 extends beyond the distal end of balloon head 16, and is slightly conical with a distal opening 46 aligned with blood flow channel 38. The purpose of distal tip 20 is to provide for atraumatic tracking over guide wire 28.

In the preferred embodiment of the present invention, reinforcing coil 42 is formed of a helically wound flat ribbon of radiopaque metal such as a stainless steel or a platinum alloy, and is bonded to the interior wall of tubing 40. In order to provide a smooth interior surface for movement of guide wire 28 and for blood flow, a coating of a thromboresistant material is preferably formed on the interior of tubing 40 and coil 42.

FIGS. 5A-5C show guide wire 28 in three different positions, representing three different stages in the use of passive perfusion balloon catheter 10. In FIG. 5A, guide wire 28 is shown extending through guide wire lumen 32, across the gap between distal opening 34 of shaft 14 and proximal opening 36 of balloon head 16, through blood flow channel 38, and out through distal opening 46 of distal tip 20.

In FIG. 5B, guide wire 28 has been withdrawn partially, so that the distal end of guide wire 28 is within guide wire lumen 32. This opens up blood flow passage 38 to allow perfusion of blood in a longitudinal direction through balloon head 16 in a proximal to distal direction. The blood flow channel 38 is sufficiently large so that balloon 18 can remain inflated for prolonged periods of time without causing significant ischemia distally from balloon 18.

FIG. 5C illustrates one of the important advantages of passive perfusion balloon catheter 10 of the present invention. In FIG. 5C, guide wire 28 is in the process of being reinserted through balloon head 16 and ultimately out through distal opening 26 in distal tip 20. This allows an exchange guide wire to be left in position across the stenosis after balloon 18 is collapsed and catheter 10 is withdrawn.

The close spacing and alignment of guide wire lumen 32 and blood flow passage 38 allows this reinsertion. Guide wire lumen 32 holds guide wire 28 in alignment, so that it can be reinserted if necessary through blood flow passage 38.

In a preferred embodiment of the present invention, distal opening 34 at the distal end of guide wire lumen 32 has a bevel angle of about 60 degrees, while proximal opening 36 at the proximal end of balloon head 16 forms a bevel angle of about 30 degrees. As illustrated in FIG. 2, the proximal tip of balloon head 16 extends slightly into guide wire lumen 32.

The purpose of the bevelled openings 34 and 36 is to provide as unobstructed a flow path as possible for blood entering blood flow channel 38. In addition, openings 34 and 36 provide a relatively smooth profile to facilitate movement of catheter 10 during insertion and removal.

FIG. 6 shows a sectional view of the distal portion of a modified embodiment of perfusion balloon catheter 10. In FIG. 6, the same reference characters used in previous Figures are used to designate similar elements. The catheter of FIG. 6 includes side port 100 in distal tip 20, which facilitates blood flow even if distal opening 46 is blocked (for example, because the artery has a sharp bend just beyond the stenosis and opening 46 is positioned against an arterial wall.

FIG. 7 shows still another embodiment in which resilient flap 120 is positioned adjacent opening 34 to urge guide wire 28 generally in a direction toward inflation lumen 30. The force applied by flap 120 further ensures that the distal tip of guide wire 28 will move out of opening 34 and through opening 36 into flow channel 38 during insertion (or reinsertion) of guide wire 28.

Passive perfusion balloon catheter 10 of the present invention has several advantages over other approaches to passive or auto perfusion. First, the large diameter of blood flow channel 38 permits relatively high blood flow rates through catheter 10 while balloon 18 is inflated. Second, flow channel 38 is relatively short compared to the lumens of other devices, which reduces the possibility of clotting. Third, because flow channel 38 is aligned with the primary flow axis of the artery, there is less trauma to the blood, and less pressure head required for blood flow. Fourth, the ability to remove guide wire 28 in order to permit perfusion, while keeping it in a position to be reinserted and left across the stenosis when catheter 10 is withdrawn offers an important option to the physician.

Although the present invention has been described with reference to preferred embodiments, workers skilled in the art will recognize that changes may be made in form and detail without departing from the spirit and scope of the invention.

What is claimed is:

1. A perfusion balloon catheter for use in combination with a guide wire to dilate a stenosed coronary artery, the perfusion balloon catheter comprising:
    an elongate shaft having an inflation lumen and a guide wire lumen integral therewith, with the guide wire lumen having a generally bevelled opening at its distal end;

a separate balloon head connected to a distal end of the shaft, the balloon head defining a relatively short blood flow channel, an open proximal end of the blood flow channel being defined by a generally bevelled opening which is opposite to, generally axially aligned with, and relatively closely longitudinally spaced from the bevelled opening at the distal end of the guide wire lumen, and the blood flow channel having a larger cross-section than the guide wire lumen;

a balloon mounted around the balloon head and defining a balloon interior which is in communication with a distal end of the inflation lumen; and a distal tip connected to and extending distally from the balloon, the distal tip having a central passage aligned with the blood flow channel to permit blood flow from the artery into the bevelled opening of the blood flow channel, through the blood flow channel and through the central passage while the balloon is inflated, and also to permit the guide wire to move through the bevelled opening of the blood flow channel, through the channel and through the central passage.

2. The catheter of claim 1 and further comprising:
a manifold connected to a proximal end of the shaft, the manifold including a guide wire port in communication with the guide wire lumen and an inflation port in communication with the inflation lumen.

3. The catheter of claim 2 wherein the manifold further includes a through port in communication with the guide wire lumen.

4. The catheter of claim 1 wherein the inflation lumen and the guide wire lumen are positioned side-by-side.

5. The catheter of claim 1 wherein the distal tip is generally tapered with a smaller diameter at its distal end than at its proximal end.

6. The catheter of claim 5 wherein the distal tip has a greater flexibility than the balloon head.

7. The catheter of claim 1 wherein the balloon and the distal tip are an integral polymeric material.

8. The catheter of claim 1 wherein the balloon has a distal segment bonded to a distal portion of the balloon head.

9. The catheter of claim 8 wherein the balloon has a proximal segment bonded to a distal portion of the shaft and a proximal portion of the balloon head.

10. The catheter of claim 9 wherein the distal portion of the shaft contains only the inflation lumen.

11. The catheter of claim 10 wherein the distal portion of the shaft has a reduced cross-section with respect to other more proximal portions of the shaft.

12. The catheter of claim 11 wherein the proximal portion of the balloon head has a reduced outer dimension with respect to more distal portions.

13. The catheter of claim 12 wherein the proximal portion of the balloon head and the distal portion of the shaft have mating surfaces which are bonded together.

14. The catheter of claim 1 wherein the balloon head comprises:
a polymeric tube which has the blood flow channel extending therethrough; and
reinforcing means for reinforcing the tube to prevent collapse of the tube which would restrict blood flow through the blood-flow channel during inflation of the balloon.

15. The catheter of claim 14 wherein the reinforcing means comprises a helically wound coil bonded to the tube.

16. The catheter of claim 15 wherein the coil is formed by a flat metal ribbon.

17. The catheter of claim 15 wherein the coil is bonded to an interior surface of the tube.

18. The catheter of claim 14 and further comprising a low friction coating on an interior surface of the tube.

19. The catheter of claim 1 wherein the distal tip further includes a side port therein.

20. The catheter of claim 1 and further comprising:
means positioned adjacent the open distal end of the guide wire lumen for guiding a guide wire toward the open proximal end of the blood flow channel.

21. The catheter of claim 20 wherein the means positioned adjacent the open distal end comprises a resilient flap attached to the shaft.

22. The catheter of claim 1 wherein a leading edge of the bevelled opening of the blood flow channel extends into and overlaps a leading edge of the bevelled opening of the guide wire lumen.

23. The catheter of claim 1 wherein the blood flow channel is only slightly longer than the balloon.

24. A perfusion balloon catheter for use in combination with a guide wire to dilate a stenosed coronary artery, the perfusion balloon catheter comprising:
an elongate shaft having an inflation lumen and a guide wire lumen integral therewith;
a separate balloon head connected to a distal end of the shaft, the balloon head defining a relatively short blood flow channel, an open proximal end of the blood flow channel being generally axially aligned with and relatively closely longitudinally spaced from an open distal end of the guide wire lumen, the balloon head including a polymeric tube which has the blood flow channel extending therethrough and reinforcing means for reinforcing the tube to prevent collapse of the tube, and with the blood flow channel having a larger cross-section than the guide wire lumen; and
a balloon mounted around the balloon head and defining a balloon interior which is in communication with the distal end of the inflation lumen.

25. The catheter of claim 24 wherein the reinforcing means comprises a helically wound coil bonded to the tube.

26. The catheter of claim 25 wherein the coil is formed by a flat metal ribbon.

27. The catheter of claim 25 wherein the coil is bonded to an interior surface of the tube.

28. The catheter of claim 25 wherein the coil is formed by a radiopaque metal.

29. The catheter of claim 24 and further comprising a low friction coating on an interior surface of the tube.

30. The catheter of claim 24 wherein the balloon has a distal segment bonded to a distal portion of the balloon head.

31. The catheter of claim 30 wherein the balloon has a proximal segment bonded to a distal portion of the shaft and a proximal portion of the balloon head.

32. The catheter of claim 31 wherein the distal portion of the shaft contains only the inflation lumen.

33. The catheter of claim 32 wherein the distal portion of the shaft has a reduced cross-section with respect to other more proximal portions of the shaft.

34. The catheter of claim 33 wherein the proximal portion of the balloon head has a reduced outer dimension with respect to more distal portions.

35. The catheter of claim 34 wherein the proximal portion of the balloon head and the distal portion of the shaft have mating surfaces which are bonded together.

36. The catheter of claim 24 wherein the balloon head has a bevelled opening at its proximal end.

37. The catheter of claim 24 wherein the guide wire lumen has a bevelled opening at its distal end.

38. The catheter of claim 24 and further comprising:
   means positioned adjacent the open distal end of the guide wire lumen for guiding a guide wire toward the open proximal end of the blood flow channel.

39. The catheter of claim 38 wherein the means positioned adjacent the open distal end comprises a resilient flap attached to the shaft.

40. The catheter of claim 24 wherein a leading edge of the open proximal end of the balloon head extends into and overlaps a leading edge of the open distal end of the guide wire lumen.

41. The catheter of claim 24 wherein the blood flow channel is only slightly longer than the balloon.

42. A method of performing angioplasty, the method comprising:
   positioning a guide wire within a patient's body so that the guide wire crosses a stenosis;
   advancing a passive perfusion balloon catheter over the guide wire until a balloon of the catheter is positioned in the stenosis, the catheter including a balloon head on which the balloon is mounted and which provides a relatively short blood flow channel through which the guide wire extends, and a separate, relatively long shaft on which the balloon head is mounted which includes an inflation lumen connected to the balloon and an internal guide wire lumen through which the guide wire extends, with the relatively short blood flow channel having a larger cross-section than the guide wire lumen;
   partially withdrawing the guide wire so that the guide wire is in the guide wire lumen but is not in the blood flow channel to permit perfusion of blood from the artery through the blood flow channel in a proximal to distal direction; and inflating the balloon.

43. The method of claim 42 and further comprising:
   readvancing the guide wire from the guide wire lumen through the blood flow channel so that the guide wire once again extends across the stenosis;
   deflating the balloon; and
   withdrawing the catheter while leaving the guide wire in position in the patient's body.

44. The method of claim 42, and further comprising the steps of:
   readvancing the guide wire from the guide wire lumen through the blood flow channel; and
   positively guiding a distal end of the guide wire into a proximal end of the blood flow channel as the guide wire is re-advanced.

* * * * *

UNITED STATES PATENT AND TRADEMARK OFFICE
CERTIFICATE OF CORRECTION

PATENT NO. : 4,944,745

DATED : July 31, 1990

INVENTOR(S) : David J. Sogard et al.

It is certified that error appears in the above-identified patent and that said Letters Patent is hereby corrected as shown below:

On the title page:

Delete [54] PERFUSION BALLOON CATHETER

Insert [54] PERFUSION BALLOON CATHETER AND METHOD OF USE THEREOF

Signed and Sealed this

Twenty-seventh Day of August, 1991

Attest:

HARRY F. MANBECK, JR.

Attesting Officer

Commissioner of Patents and Trademarks